(12) United States Patent
Huang et al.

(10) Patent No.: US 11,013,844 B2
(45) Date of Patent: May 25, 2021

(54) TREATMENT DEVICE FOR PLASMA VIRUS INACTIVATION

(71) Applicants: City of Hope, Duarte, CA (US); Shanghai Blood Center, Shanghai (CN)

(72) Inventors: Yuwen Huang, Duarte, CA (US); Qin Mo, Duarte, CA (US); Bo Zhang, Duarte, CA (US); Kaicheng Qian, Duarte, CA (US); Yongming Zhu, Duarte, CA (US); Shirong Wang, Duarte, CA (US); Xun Wang, Duarte, CA (US); Xiaofei Wu, Duarte, CA (US); Yao Jia, Duarte, CA (US); Lidong Liu, Duarte, CA (US)

(73) Assignees: City of Hope, Duarte, CA (US); Shanghai Blood Center, Shanghai (CN)

(*) Notice: Subject to any disclaimer, the term of this patent is extended or adjusted under 35 U.S.C. 154(b) by 339 days.

(21) Appl. No.: 14/946,285

(22) Filed: Nov. 19, 2015

(65) Prior Publication Data

US 2016/0144095 A1 May 26, 2016

(30) Foreign Application Priority Data

Nov. 20, 2014 (CN) .................. 201410667647.X
Nov. 20, 2014 (CN) .................. 201420700689.4

(51) Int. Cl.
*A61M 1/34* (2006.01)
*A61M 1/36* (2006.01)

(52) U.S. Cl.
CPC ........ *A61M 1/3496* (2013.01); *A61M 1/3683* (2014.02)

(58) Field of Classification Search
CPC .................. A61M 1/3496; A61M 1/3683
USPC ........................................... 435/1
See application file for complete search history.

(56) References Cited

U.S. PATENT DOCUMENTS

| 5,104,373 A | * | 4/1992 | Davidner | ............... A61M 1/36 604/6.08 |
| 2004/0127840 A1 | * | 7/2004 | Gara | .................. A61M 1/3683 604/4.01 |
| 2013/0178834 A1 | * | 7/2013 | Greenberg | .......... A61M 1/3621 604/522 |

FOREIGN PATENT DOCUMENTS

| CN | 1239952 | * | 4/2000 | ............... A61L 2/08 |
| CN | 2440516 Y | * | 8/2001 | ............... A61L 2/16 |

OTHER PUBLICATIONS

Liu, Xiaoying, et. al. "Photochemically inactivated hepatitis B virus promotes upregulation of Th1-type cytokines." *Photochemistry and Photobiology*, vol. 88, No. 5, 2012, pp. 1287-1292.
Politis, C., et. al. "Haemovigilance data on the use of methylene blue virally inactivated fresh frozen plasma with the Theraflex MB-Plasma System in comparison to quarantine plasma: 11 years' experience." *Transfusion Medicine*, vol. 24, No. 5, 2014, pp. 316-320.
Schlenke, P. "Pathogen inactivation technologies for cellular blood components: an update." *Transfusion Medicine and Hemotherapy*, vol. 41, No. 4, 2014, pp. 309-325.
Steinmann, E., et. al. "Two pathogen reduction technologies—methylene blue plus light and shortwave ultraviolet light—effectively inactivate hepatitis C virus in blood products." *Transfusion*, vol. 53, No. 5, 2013, pp. 1010-1018.

* cited by examiner

*Primary Examiner* — Nghi V Nguyen
*Assistant Examiner* — Natalie M Moss
(74) *Attorney, Agent, or Firm* — Mintz Levin Cohn Ferris Glovsky and Popeo, P.C.

(57) ABSTRACT

A device and method can be used for clinical virus inactivation treatment to automatically, continuously and cyclically treat plasma of a patient in a closed system. The disclosed plasma treatment device may be used for an anti-viral agent such as, for example, methylene blue photochemical plasma virus inactivation. The plasma treatment device can perform real-time treatment to the plasma in the closed system on the basis of the principle of plasma exchange and can realize real-time back-transfusion during treatment.

19 Claims, 2 Drawing Sheets

TREATMENT DEVICE FOR PLASMA VIRUS INACTIVATION

REFERENCE TO PRIORITY DOCUMENT

This application claims priority to co-pending Chinese Patent Applications Serial Numbers 201410667647.x, and 201420700689.4 both entitled "TREATMENT DEVICE FOR PLASMA VIRUS INACTIVATION" and filed on Nov. 20, 2014. Priority to the aforementioned filing date is claimed and the patent applications are incorporated herein by reference in its entirety.

BACKGROUND

The present disclosure relates to the technical field of medical treatment, in particular to a treatment device for plasma virus inactivation.

The main role of plasma is to carry blood cells and transport substances for maintaining human body living activities, wastes produced in the body, and the like. Plasma is equivalent to an intercellular substance of connective tissues. Plasma is an important component of blood and is a light yellow liquid (because it contains bilirubin). Water accounts for 90-92% of the chemical components of plasma. The other 10% of the chemical components mainly includes solute plasma protein, electrolytes, nutrients, enzymes, hormones, cholesterol and other important components.

Plasma virus inactivation (also referred to as virus deactivation) refers to a process of destroying the structure of virus protein by physical or chemical means to enable viruses possibly existing in plasma to lose infective, pathogenic and reproductive abilities. In the past ten years, many plasma virus inactivation techniques have already been applied and popularized in many developed countries including China. Due to reliable virus inactivation effect and safety, methylene blue photochemical plasma virus inactivation has become the most widely applied technique in this field in recent years.

The chemical name of methylene blue is 3,7-bis(dimethylamino)phenothiazin-5-ium chloride. It is also referred to as "royal blue". Methylene blue is an aromatic heterocyclic compound. The CAS number of methylene blue is 61-73-4. The aqueous solution of methylene blue is blue in an oxidative environment and can be reduced to a colorless state when contacted with reducing agents such as zinc and ammonia water. After being intravenously injected, methylene blue has a quick effect, is drained with urine substantially without going through metabolism, can be absorbed orally under gastrointestinal tract pH conditions, and is quickly reduced to white methylene blue within tissues. Within 6 days, 74% of methylene blue is drained through urine, wherein 22% is in the original form, the other is white methylene blue, part of which can be methylated, and a small amount of methylene blue is drained through bile and feces.

SUMMARY

The existing plasma virus inactivation technique is only applicable to the treatment of a single bag of plasma and cannot be used for large-scale and continuous treatment of plasma of patients. In view of this, disclosed herein is an improved device and method that can be used for clinical virus inactivation treatment and that can automatically, continuously and cyclically treat plasma of a patient in a closed system to achieve the goal of specific treatment. In another embodiment, the device can automatically, intermittently and cyclically treat plasma of a patient in a closed system. The disclosed plasma treatment device may be used for an anti-viral agent such as, for example, methylene blue photochemical plasma virus inactivation. The plasma treatment device can perform real-time treatment to the plasma in the closed system on the basis of the principle of plasma exchange, and can realize real-time back-transfusion during treatment. The disclosed device also greatly improves the treatment capacity and the treatment efficiency over existing systems and has a wide application prospect.

In an embodiment, treatment device for plasma virus inactivation comprises a blood separation device and a light treatment device that are coupled to one another in a single treatment device for plasma virus inactivation. The blood separation device and the light treatment device are respectively provided with an input port and an output port, the output port of the blood separation device is connected with the input port of the light treatment device through a first conduit, the first conduit is provided with a first transport pump and a dosing device thereon, the treatment device for plasma virus inactivation further comprises a second conduit and a third conduit, the output port of the light treatment device and the input port of the blood separation device are respectively connected with one end of the second conduit and one end of the third conduit, the second conduit is provided with a second transport pump thereon and the third conduit is provided with a third transport pump thereon.

Free ends of the second conduit and the third conduit in use can be simultaneously communicated with a blood sample supply system. Under this situation, the blood sample supply system can be a blood output person (i.e., a human). The free ends of the second conduit and the third conduit can also be respectively communicated with a blood supply system and a blood collection system. Under this situation, the blood supply system and the blood collection system can be respectively containers for containing blood products and collecting blood products.

In an embodiment, the light treatment device comprises an illumination pipeline and a light source for illuminating the illumination pipeline, and an input port and an output port of the illumination pipeline are respectively the input port and the output port of the light treatment device. The light treatment device can further comprise a box body, and both the light source and the illumination pipeline are located within the box body. The light treatment device further can comprise a temperature control device for controlling the temperature of the internal space of the box body. The illumination pipeline can comprise an illumination container and/or illumination guide pipe. The illumination guide pipe can be in a tortuous shape with a plurality of straight segments. The illumination pipeline can be further provided with an oscillating device thereon.

The dosing device can be a dosing device that doses an antiviral agent, such as for example solid methylene blue or liquid methylene blue. The device is described herein in the example context of dosing solid methylene blue or liquid methylene blue although it is not limited to dosing solid methylene blue or liquid methylene blue. In an embodiment, the methylene blue dosing device comprises a medicine loading container with a hollow chamber and a medicine loading film, the medicine loading film is located within the medicine loading container, and the medicine loading container is provided with an inlet and an outlet. The medicine loading container can include of a lower bottom with an inlet and a corresponding upper bottom with an outlet, and the medicine loading film is located at an inlet of the hollow chamber.

The medicine loading film is can be in a hemispherical shape, medicines are filled within a recess formed by the hemispherical shape, and the opening of the hemispherical shape and the flow direction of liquid in the dosing device are kept to be horizontal.

The first conduit between the blood separation device and the dosing device can be provided with a shutoff valve, and the first conduit between the dosing device and the light treatment device is provided with a shutoff valve. A plurality of dosing devices can be connected in parallel on the first conduit, inlet pipelines of the dosing devices are respectively provided with shutoff valves, and the first conduit between the dosing device and the light treatment device is provided with a shutoff valve.

The second conduit between the second transport pump and the light treatment device is further provided with a buffer device. The second conduit between the light treatment device and the buffer device can be further provided with a shutoff valve, and the second conduit between the buffer device and the second transport pump is further provided with a shutoff valve.

The treatment device further comprises a liquid replenishing bag, and an output port of the liquid replenishing bag is connected with an inlet of the second transport pump. A conduit between the liquid replenishing bag and the second transport pump can be further provided with a shutoff valve. The third transport pump is a two-way pump, and the third conduit is a two-way conduit in an embodiment.

The third conduit and the third transport pump mainly operate in a manner such that the collected blood samples are firstly delivered into the blood separation device through the third conduit, the blood separation device performs centrifugal separation to the blood samples, then the plasma is guided out through the output port, and the remaining part is transfused back through the third conduit. The third conduit is provided with a shutoff valve thereon. Each of the transport pumps and each of the shutoff valves are electrically connected with a central control system.

In the plasma treatment device, the shutoff valves and pumps play a role of controlling liquid flow between the devices, and each transport pump and each shutoff valve can be independently controlled and operated, and can also be integrally controlled and operated through the central control system.

In another aspect, a plasma treatment device is used in methylene blue photochemical plasma virus inactivation. In another aspect, there is disclosed a method of performing plasma virus inactivation, comprising: flowing blood from a source through a first fluid conduit into a blood separation device; automatically separating the blood into plasma and a remaining portion; flowing the plasma from the blood separation device through a second fluid conduit and through a blood dosing device that doses an antiviral agent into the plasma; automatically flowing the plasma from the blood dosing device into an illumination pipeline of a light treatment device and illuminating the plasma using a light source coupled to the illumination pipeline; and transfusing the plasma to the source.

As described above, the plasma treatment device provided by the present disclosure is mainly used for methylene blue photochemical plasma virus inactivation, is a system for performing real-time treatment to plasma on the basis of the principle of plasma exchange, can realize real-time back-transfusion while treatment, greatly improves the treatment capacity and treatment efficiency, and has a wide application prospect.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
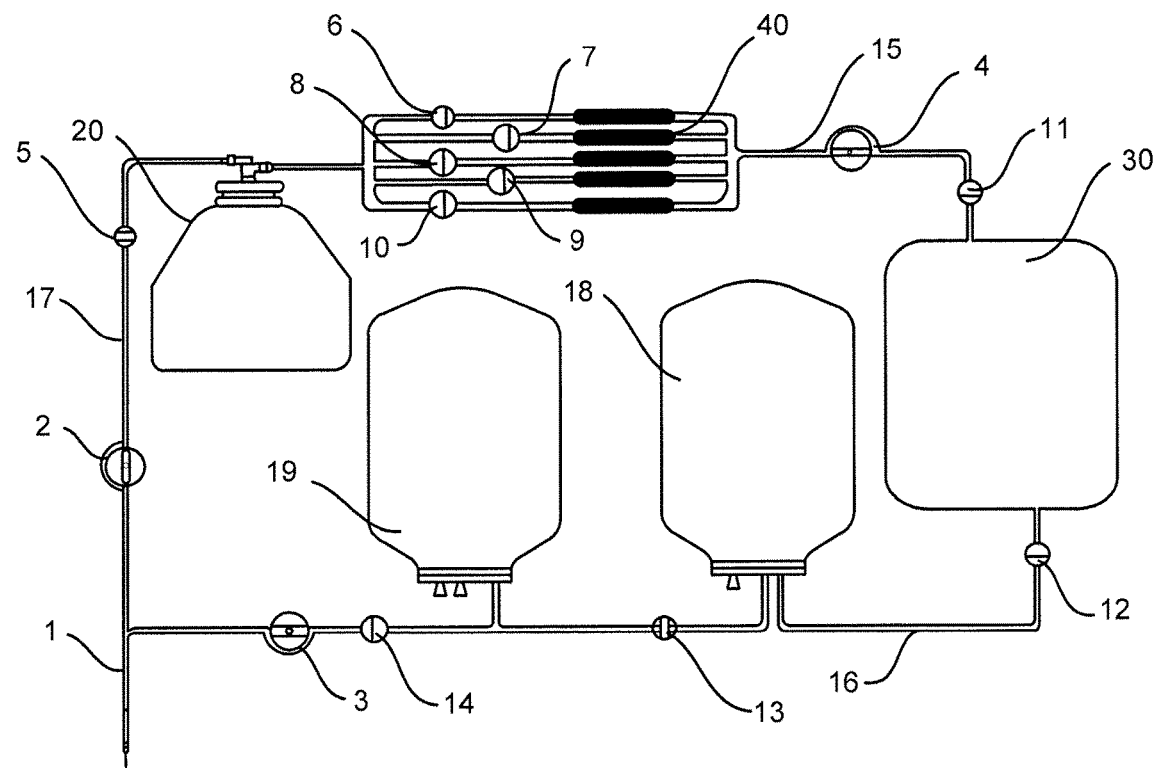
FIG. 1 illustrates a schematic view of a treatment device.

Before the present subject matter is further described, it is to be understood that this subject matter described herein is not limited to particular embodiments described, as such may of course vary. It is also to be understood that the terminology used herein is for the purpose of describing particular embodiments only, and is not intended to be limiting. Unless defined otherwise, all technical terms used herein have the same meaning as commonly understood by one skilled in the art to which this subject matter belongs.

The embodiments of the present disclosure will be described below through specific examples. One skilled in the art can easily understand other advantages and efficacies of the present disclosure according to contents disclosed by the description. The present disclosure can also be implemented or applied through other different specific embodiments. Various modifications or changes can be made to all details in the description based on different points of view and applications without departing from the spirit of the present disclosure.

It shall be known that process apparatuses or devices which are not specifically indicated in the following embodiments are common apparatuses or devices in the field; and all pressure values and ranges refer to absolute pressure.

In addition, it shall be understood that, unless otherwise stated, one or more of the method steps mentioned in the present disclosure does not exclude the situation that other method steps may exist before and after the combined steps or other method steps may be interposed between such clearly mentioned steps; and it shall be also understood that, unless otherwise stated, a combined connecting relation between one or more of apparatuses/devices mentioned in the present disclosure does not exclude the situation that other apparatuses/devices may exist before and after the combined apparatuses/devices or other apparatuses/devices may be interposed between two apparatuses/devices. In addition, unless otherwise stated, the serial number of each method step is only used as a convenient tool for distinguishing the method steps instead of limiting the arrangement sequence of the method steps or limiting the implementable range of the present disclosure, and the change or adjustment of relative relations thereof shall be viewed as falling in the implementable range of the present disclosure under the situation that the technical contents are substantively not changed.

The term "antiviral agent" as provided herein refers to an agent (e.g., nucleic acid, compound, polypeptide) that is capable of inhibiting the activity (e.g., transcription, translation, replication, infectivity) of a virus. Useful antiviral agents include, but are not limited to, antiviral RNAs, protease inhibitors, nucleoside reverse transcriptase inhibitors, non-nucleoside reverse transcriptase inhibitors and nucleoside analogs. In embodiments the antiviral agent is an inhibitor of viral replication. In embodiments, the antiviral agent is an inhibitor of viral transcription. In embodiments, the antiviral agent is an inhibitor of viral entry. In embodiments, the antiviral agent is an inhibitor of viral transport. In embodiments, the antiviral agent is an inhibitor of viral packaging. In embodiments, the antiviral agent binds to a target viral nucleic and reduces transcription of the target viral nucleic acid or reduces the translation of the target viral nucleic acid (e.g., mRNA) or alters transcript splicing. In embodiments, the antiviral agent is a nucleic acid (i.e. antiviral RNA) that is capable of binding (e.g., hybridizing) to a target viral nucleic acid (e.g., an Rev RNA) and reducing translation of the target viral nucleic acid. The target viral nucleic acid is or includes one or more target nucleic acid sequences to which the antiviral agent binds (e.g., hybridizes). In embodiments, the antiviral agent is or includes a sequence that is capable of hybridizing to at least a portion of a target viral nucleic acid at a target viral nucleic acid sequence. Non-limiting examples of antiviral agents include antiviral nucleic acids, such as siRNAs, ribozymes, RNA decoys, snoRNAs and shRNAs; and chemical compounds, such as zidovudine, acyclovir, ganciclovir, vidarabine, idoxuridine, trifluridine, levovirin, viramidine, ribavirin, foscarnet, amantadine, rimantadine, saquinavir, indinavir, amprenavir, lopinavir and ritonavir.

As defined herein, the term "inhibition", "inhibit", "inhibiting" and the like in reference to a protein-inhibitor (e.g., compound) interaction means negatively affecting (e.g., decreasing) the activity or function of the protein (e.g., decreasing activity of a viral transcription factor) relative to the activity or function of the protein in the absence of the inhibitor (e.g., compound). In some embodiments inhibition refers to reduction of a disease or symptoms of disease. In some embodiments, inhibition refers to a reduction in the presence of a disease-related agent (e.g., an infectious agent, infectious agent resistant to one or more antiviral inhibitors). Thus, inhibition includes, at least in part, partially or totally blocking stimulation, decreasing, preventing, or delaying activation, or inactivating, desensitizing, or down-regulating signal transduction or enzymatic activity or the amount of a protein. Similarly an "inhibitor" is a compound that inhibits viral survival, growth, or replication, e.g., by binding, partially or totally blocking, decreasing, preventing, delaying, inactivating, desensitizing, or down-regulating enzymatic activity (e.g., strand transfer during viral integration).

Non-limiting examples of viruses target by the antiviral agents provided herein include influenza virus, human immunodeficiency virus ("HIV"), herpes simplex virus ("HSV", type 1 or 2), human papilloma virus ("HPV", type 16 or 18), human cytomegalovirus ("HCMV") or human hepatitis B or C virus ("HBV", Type B; "HCV", type C).

FIG. 1 shows a schematic view of a blood treatment device for plasma virus inactivation. The treatment device includes a blood separation device 20 having an input port and an output port, and a light treatment device 30 having an input port and an outport port. A first fluid conduit 15 fluidly connects the output port of the blood separation device to the input port of the light treatment device 30. A transport pump 4 is positioned along the first fluid conduit 15 and is configured to pump fluid through the first fluid conduit 15 such as toward the light treatment device 30. In addition, a shut off valve 11 is positioned along the first fluid conduit 15 and can be activated to shut off fluid flow through the first fluid conduit 15. In addition, a dosing device 40 is fluidly coupled to the first fluid conduit 15 in the flow pathway between the blood separation device 20 and the light treatment device 30. Thus, fluid flows from the blood separation device 20 to the light treatment device 30 through the dosing device 40. The dosing device 40 is described in more detail below.

With reference still to FIG. 1, the blood treatment device further includes a second fluid conduit 16 that is fluidly connected to an output port of the light treatment device 30. A second transport pump 3 is positioned along the second fluid conduit 16 and is configured to pump fluid through the second fluid conduit 16. In addition, the blood treatment device further includes a third fluid conduit 17 that is fluidly connected to an input port of the blood separation device 20. A third transport pump 2 is positioned along the third fluid conduit 17 and is configured to pump fluid therethrough. A shut off valve 5 is also positioned along the third fluid conduit 17. Each of the second conduit 16 and the third conduit 17 has a free end 1 or an open end that can be connected to a source of blood or a destination of blood, as described in more detail below.

The blood treatment device further includes a buffer device 18 along the second fluid conduit 16. The buffer device 18 is fluidly connected to an output of the light treatment device 30. In addition, a replenishing container, such as a replenishing bag 19, is also positioned along the second fluid conduit 16 downstream of the buffer device 18. A shut off valve 12 is positioned along the second fluid conduit between the light treatment device 30 and the buffer device 18. Another shut off valve 13 is positioned along the second fluid conduit 16 between the buffer device 18 and the replenishing bag 19. Finally, a shut off valve 14 is also positioned between the replenishing bag 19 and the second transport pump 3. The shutoff valves include mechanisms that can be activates to shut off fluid flow through a respective fluid conduit.

Thus, as shown in FIG. 1, the present disclosure provides a treatment device for plasma virus inactivation, which comprises a blood separation device 20 and a light treatment device 30, wherein the blood separation device 20 and the light treatment device 30 are respectively provided with an input port and an output port, the output port of the blood separation device 20 is connected with the input port of the light treatment device 30 through a first conduit 15, the first conduit 15 is provided with a first transport pump 4 and a dosing device 40 thereon, the treatment device for plasma virus inactivation further comprises a second conduit 16 and a third conduit 17, the output port of the light treatment device 30 and the input port of the blood separation device 20 are respectively connected with one end of the second conduit 16 and one end of the third conduit 17, the second conduit 16 is provided with a second transport pump 3 thereon, and the third conduit 17 is provided with a third transport pump 2 thereon. The third conduit 17 can be a two-way conduit that provides for fluid to flow in opposite directions through the third conduit 17. In addition, the transport, along with third conduit can be a two-way pump that is configured to flow fluid in one or two directions through the conduit.

The blood separation device 20 (or blood separation instrument) is configured to separate plasma from blood cells such as through centrifugal effect, wherein the blood cells can be transfused back to a patient and the plasma is subjected to subsequent treatment by the treatment device. The blood separation device includes mechanical components that provide a centrifugal force to blood to separate plasma cells from blood cells. One skilled in the art can select a blood separation instrument or instruments of proper models and separation conditions according to experiences. Specific applicable blood separation instruments include blood cell separators of American Baxter Company and Haemonalics Company. Specific separation conditions can be with reference to product instructions and/or through experience of a person of ordinary skill.

Blood samples enter the blood separation device 20 through a free end 1 of the third conduit 17. The transport pump 2 provides a pressure differential that propels blood through the third conduit 17 toward the blood separation device. The blood flows through the third conduit into the blood separation device 20 which acts on the blood to separate plasma cells from blood cells. The plasma obtained after treatment by the blood separation device 20 flows out of the output port into the first conduit 15 toward the dosing device 40 and the light treatment device 30.

The remaining part of the blood that does not flow through the outlet port of the blood separation device 20 is fed back into the third conduit 17 from the blood separation device. As mentioned, the third conduit 17 is a two-way conduit and the third transport pump 2 on the third fluid conduit is a two-way pump that can propel fluid in two separate directions. The third conduit 17 is provided with a shutoff valve 5 thereon. In this manner, blood can flow into the blood separation device 20, which separates the blood into plasma cells and blood cells. Plasma cells flow through the first conduit 15 toward the dosing device in 40. The remaining portion of the blood flows back out of the blood separation device 20 through the third conduit 17 and toward the free end 1.

The free ends 1 of the second conduit 16 and the third conduit 17 in use can be simultaneously or individually communicated or otherwise fluidly connected with a blood sample supply system. Under this situation, the blood sample supply system can be a blood output person (e.g., a human that is fluidly connected to the free end 1, such as via an IV port) and the remaining part of the blood samples can be transfused back to the blood output person through the third conduit 17. The free ends 1 of the second conduit 16 and the third conduit 17 can also be respectively communicated or otherwise fluidly connected with a blood supply system and a blood collection system. Under this situation, the blood supply system and the blood collection system can be respectively containers for containing blood products and collecting blood products, and the remaining part of the blood samples can be input into the container through the third conduit 17 and are collected in the container for future use.

In example embodiments, the first fluid conduit 15 can be provided with only a single dosing device 40 thereon, and/or a plurality of dosing devices 40 can also be connected in parallel on the first conduit 15. When only one dosing device is provided, the first conduit 15 between the blood separation device 20 and the dosing device 40 is provided with a single shutoff valve 6, and the first conduit 15 between the dosing device 40 and the light treatment device 30 is provided with a shutoff valve 11. The shutoff valve 6 and the shutoff valve 11 thus control fluid flow between the blood separation device 20 and the light treatment device 30.

In another embodiment, the dosing device 40 is supplemented with or replaced by a manual injection of the antiviral agent by a user. For example, the first fluid conduit may include an injection port that permits a user to insert a syringe or such device into the first fluid conduit. The user then injects a desired amount of antiviral agent into the first fluid conduit.

When a plurality of dosing devices 40 are connected in parallel to the first fluid conduit 15, the structure thereof is as shown in FIG. 1. A plurality of dosing devices 40, each having a respective fluid conduit for blood to flow therethrough, is connected in parallel on the first conduit 15. That is, the first fluid conduit includes two or more dosing devices connected in parallel along the first fluid conduit. Each dosing device number 40 includes a fluid conduit formed of an inlet pipeline through which plasma flows. Each pipeline is provided with a respective shutoff valve 6, 7, 8, 9, 10. The first conduit 15 between the dosing device 40 and the light treatment device 30 is also provided with a shutoff valve 11. In the example shown in FIG. 1, there are five dosing devices 40 each having a dedicated pipeline and shutoff valve. It should be appreciated that the quantity of dosing devices 40 can vary.

Figure 2:
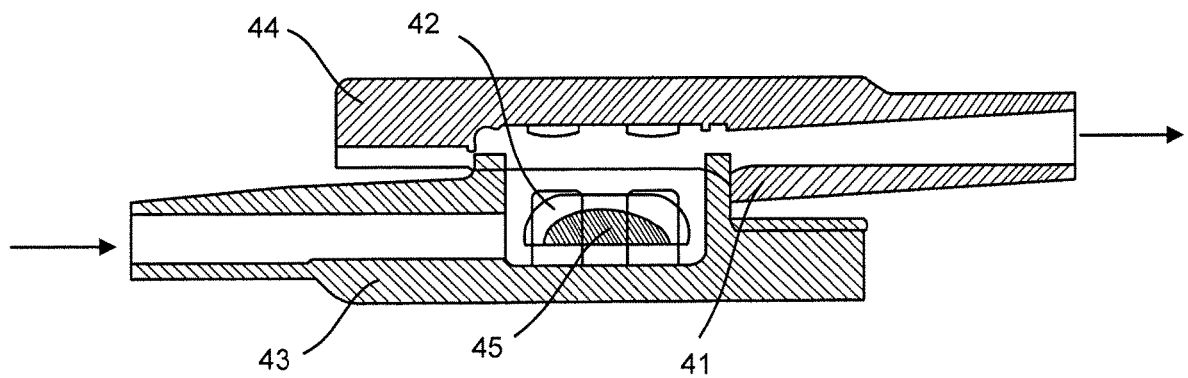
FIG. 2 illustrates a schematic view of a structure of a dosing device of the treatment device.

The dosing device 40 can be a solid dosing device and can also be a liquid dosing device. The dosing device can be any type of device that is configured to dose a substance to blood. As shown in the schematic view of FIG. 2, in an example embodiment the dosing device 40 is a solid dosing device (such as a membrane adsorption methylene blue dosing device). In an embodiment, the dosing device 40 includes a medicine (or antiviral agent) loading container 41 that defines a hollow chamber. The dosing device 40 includes a medicine loading film 42 located within the medicine loading container 41. In addition, the medicine loading container 41 includes an inlet and an outlet. The medicine loading container 41 is at least partially formed of a lower bottom 43 with an inlet and a corresponding upper bottom 44 with an outlet. The medicine loading film 42 is located at an inlet of the hollow chamber. In an exemplary embodiment, the medicine loading film 42 is in a hemispherical shape that forms a recess or any shape configured to support a fluid. This permits medicines to be filled within a recess formed by the hemispherical shape. An opening of the hemispherical shape and a flow direction of liquid in the dosing device 40 are kept to be horizontal.

As described above, the free end 1 of the third conduit 17 can be directly connected with a container for collecting the blood products. The blood products can be guided out from the third conduit 17 at a higher flow rate. However, theoretically, the plasma obtained after treatment through the light treatment device 30 can be directly used for back-transfusion. Since a back-transfusion target may be a blood output person, the back-transfusion speed is desirably not too fast.

In addition, in order to further improve efficiency, the present disclosure can further comprise a buffer device 18 formed of a container that can contain a fluid. The buffer device 18 is positioned along and fluidly connected to the second conduit 16 between the second transport pump 3 and the light treatment device 40. This permits fluid to flow into an inlet of the buffer device 18 from the third conduit 16 and then back into the third conduit 16 through an outlet of the buffer device 18. During actual operation, the plasma obtained after treatment can be guided to and firstly stored in the buffer device 18. Then back-transfusion is performed, and the light treatment device 40 can be continuously used for subsequent plasma treatment. As shown in FIG. 1, the second conduit 16 between the light treatment device 40 and the buffer device 18 is further provided with a shutoff valve 12, and the second conduit 16 between the buffer device 18 and the second transport pump 3 is further provided with a shutoff valve 13, as mentioned above.

A liquid replenishing bag 19 or other container is positioned along the second conduit 16. The replenishing bag defines a chamber in fluid communication with the second conduit 16. The liquid replenishing bag 19 plays a role of preventing blood from being coagulated and blocking a needle, which may be located at the free end 1. As shown in FIG. 1, an output port of the liquid replenishing bag 19 is connected with an inlet of the second transport pump 3, and a conduit between the liquid replenishing bag 19 and the second transport pump 3 is further provided with a shutoff valve 14. The liquid replenishing bag 19 can contain a liquid that can be flowed into the second conduit 16 to add liquid from the replenishing bag to the plasma.

Figure 3:
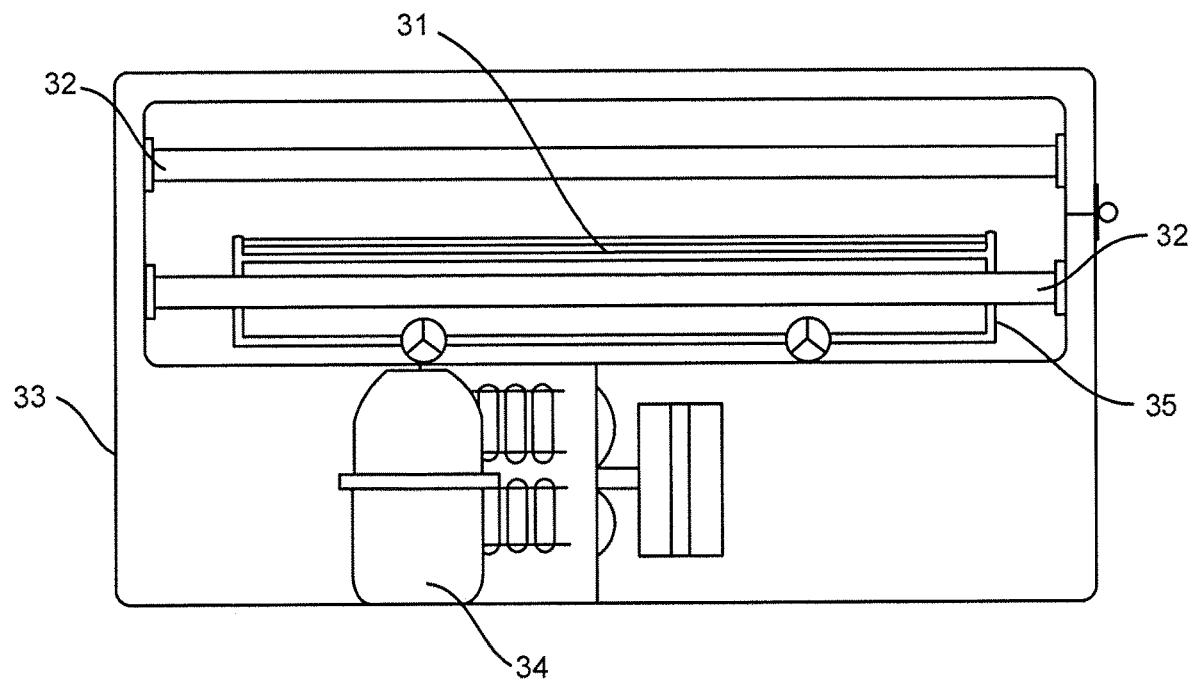
FIG. 3 illustrates a schematic view of a structure of a light treatment device of the treatment device.

As shown in FIG. 3, the light treatment device 30 comprises an illumination pipeline 31 and at least one light source 32 for illuminating the illumination pipeline 31. The light source can vary and can have a specific illumination, for example of 30000-38000 Lx. The illumination pipeline 31 includes an input port and an output port which form the input port and the output port of the light treatment device 30. The light treatment device 30 further includes a housing or box body 33 and also includes a temperature control device 34 that controls the temperature of the internal space of the box body 33. Any type of temperature control device can be used.

Both the light source 32 and the illumination pipeline 31 are located within the box body 33. In an example embodiment, the internal temperature range of the box body is generally 2-8° C. The illumination pipeline 31 comprises an illumination container and/or illumination guide pipe. When the illumination pipeline 31 is an illumination container, the plasma can be placed in the illumination container (via the first fluid conduit) for illumination. When the illumination pipeline 31 is an illumination guide pipe, the plasma can be illuminated by using the light source 32 when the plasma flows through the illumination guide pipe. In order to save the space and improve the illumination efficiency, generally the illumination guide pipe can have a tortuous shape or undulating shape with a plurality of straight segments. That is, it defines a flow pathway with a tortuous shape that includes at least one curved pathway and at least one straight pathway. The position of the light source 32 can be matched with the illumination pipeline 31 as much as possible, so as to guarantee or increase the likelihood that the light emitted by the light source 32 can fully illuminate the illumination pipeline 31. A plurality of light sources 32 can be arranged so as to guarantee or increase the likelihood that the illumination pipeline 31 can be illuminated by light from a plurality of directions. No matter what illumination manner is adopted, the illumination time for the plasma can be guaranteed and the illumination time is generally 30-60 min, in a non-limiting example. The illumination pipeline 31 can be further provided with an oscillating device 35 thereon, so as to guarantee or increase the likelihood that the plasma in the illumination pipeline 31 can be uniformly illuminated.

In the present disclosure, the shutoff valves and pumps play a role of controlling liquid flow between the devices, and each transport pump and each shutoff valve can be independently controlled and operated and can also be integrally controlled and operated through the central control system. Each transport pump and each shutoff valve are electrically connected with the central control system, which can be formed of both hardware and software.

In use, blood flows into the blood separation device 20 from a source through the third conduit 17. The blood is separated through the blood separation device 20 to result in plasma and a remaining portion. Plasma flows toward enters the light treatment device 30 through the first conduit 15. The remaining portion of the blood is automatically transfused back through the third conduit 17 toward the source. When the plasma passes through the first conduit 15, it flows into the dosing device 40, which automatically adds the antiviralagent into the plasma. In an alternate embodiment, a user manually adds the antiviralagent into the plasma.

The plasma flows into the illumination pipeline 31, which is a tortuous illumination guide pipe with a plurality of straight segments. The light treatment device 20 automatically subjects the plasma to illumination treatment when the plasma flows through the illumination guide pipe after the plasma enters the light treatment device 30. As an example, specific conditions include a temperature of 2-8° C., 30000-38000Lx illumination treatment for 30-60 min when the plasma is in the light treatment device 30. The plasma subjected to illumination treatment flows out of the light treatment device 30 to the buffer device 18 and then is subjected to back-transfusion operation through the buffer device 18. The liquid replenishing bag 19 can replenish liquid at proper time, so as to prevent the blood from being coagulated and blocking the needle, which is connected to the free end 1.

As described above, the plasma treatment device can be used for methylene blue photochemical plasma virus inactivation. The device performs real-time treatment to plasma on the basis of the principle of plasma exchange and it performs real-time back-transfusion. The device greatly improves the treatment capacity and treatment efficiency with respect to existing systems.

While this specification contains many specifics, these should not be construed as limitations on the scope of an disclosure that is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

The invention claimed is:

1. A treatment device for plasma virus inactivation, comprising:

a blood separation device having an input port and an output port, the blood separation device including a mechanism that separates blood into plasma and a remaining portion;
a light treatment device having an input port and an output port;
a first fluid conduit that fluidly connects the output port of the blood separation device with the input port of the light treatment device so that plasma from the blood separation device can flow to the light treatment device through the first fluid conduit, wherein the first fluid conduit is directly connected at a first end to the output port of the blood separation device and at a second end to the input port of the light treatment device;
a first transport pump coupled to the first fluid conduit and configured to pump fluid through the first conduit, the first transport pump being positioned on the first conduit between the blood separation device and the light treatment device;
a plurality of dosing devices coupled to the first fluid conduit at a location between the blood separation device and the light treatment device so that plasma flows through the plurality of dosing devices as plasma flows from the blood separation device to the light treatment device, wherein at least one of the dosing device doses an antiviral agent into the plasma, wherein the first fluid conduit branches only at a first single location into at least two parallel flow pathways, each of the at least two parallel flow pathways containing one of the plurality of dosing devices, and wherein the at least two parallel flow pathways converge only at a single second location into a single and sole fluid passageway that fluidly connects only to the input port of the light treatment device;
a second fluid conduit fluidly connected to the outlet port of the light treatment device;
a third fluid conduit fluidly connected to the input port of the blood separation device;
a second transport pump coupled to the second fluid conduit and configured to pump fluid through the second conduit, the second transport pump located on the second fluid conduit downstream of the light treatment device; and
a third transport pump coupled to the third fluid conduit and configured to pump fluid through the third conduit,
wherein at least one of the dosing devices comprises a medicine loading container formed of a lower structure positioned beneath an upper structure that collectively define a chamber therebetween, the lower structure entirely forming a fluid inlet and an inlet passageway and the upper structure entirely forming a fluid outlet and an outlet passageway, wherein fluid flows into the dosing device via the fluid inlet, through the chamber, and out of the dosing device via the fluid outlet, and wherein a medicine loading film is located within the chamber, the medicine loading film comprising a hemispherical shape that forms a recess configured to support a fluid to permit medicine to be filled within the recess.

2. The treatment device according to claim 1, wherein the light treatment device comprises an illumination pipeline and a light source that illuminates the illumination pipeline, and wherein an input port of the illumination pipeline is the input port of the light treatment device, and wherein an output port of the illumination pipeline is the output port of the light treatment device.

3. The treatment device according to claim 2, wherein the light treatment device further comprises a box body, and wherein both the light source and the illumination pipeline are located within the box body.

4. The treatment device according to claim 3, wherein the light treatment device further comprises a temperature control device that controls a temperature of an internal space of the box body.

5. The treatment device according to claim 2, wherein the illumination pipeline comprises at least one of an illumination container and an illumination guide pipe.

6. The treatment device according to claim 5, wherein the illumination guide pipe is in a tortuous shape with a plurality of straight segments.

7. The treatment device according to claim 2, wherein the illumination pipeline includes an oscillating device.

8. The treatment device according to claim 1, wherein the antiviral agent of the dosing device is solid methylene blue or liquid methylene blue.

9. The treatment device according to claim 1, wherein the first conduit includes a first shutoff valve located between the blood separation device and the plurality of dosing devices, and the first conduit also includes a second shutoff valve located between the at least one dosing device and the light treatment device.

10. The treatment device according to claim 1, wherein the second conduit is fluidly connected to a buffer device.

11. The treatment device according to claim 1, further comprising a liquid replenishing bag having an output port fluidly connected with an inlet of the second transport pump.

12. The treatment device according to claim 11, wherein a conduit between the liquid replenishing bag and the second transport pump includes a shutoff valve.

13. The treatment device according to claim 1, wherein the third transport pump is a two-way pump, and the third conduit is a two-way conduit.

14. The treatment device according to claim 13, wherein the third conduit includes a shutoff valve thereon.

15. The treatment device according to claim 1, further comprising a central control system that controls the transport pumps.

16. The treatment device according to claim 1, wherein each of the at least two parallel flow pathways includes a dedicated shut off valve at a location between the first single location and the second single location such that parallel flow pathways include a plurality of dedicated shut off valves.

17. The treatment device according to claim 1, wherein a flow direction of fluid relative to the hemispherical shape is horizontal.

18. The treatment device according to claim 17, wherein the fluid inlet of the dosing device extends along a first axis and the fluid outlet of the dosing device extends along a second axis that is offset from the first axis, and wherein both the first axis and the second axis are horizontal.

19. The treatment device according to claim 18, wherein the second axis is positioned entirely above the medicine loading film.

* * * * *